(12) United States Patent
Ochs et al.

(10) Patent No.: US 9,880,125 B2
(45) Date of Patent: Jan. 30, 2018

(54) MICROMECHANICAL SENSOR DEVICE

(71) Applicant: Robert Bosch GmbH, Stuttgart (DE)

(72) Inventors: Thorsten Ochs, Schwieberdingen (DE); Denis Kunz, Untergruppenbach (DE)

(73) Assignee: Robert Bosch GmbH, Stuttgart (DE)

( * ) Notice: Subject to any disclaimer, the term of this patent is extended or adjusted under 35 U.S.C. 154(b) by 681 days.

(21) Appl. No.: 14/267,472

(22) Filed: May 1, 2014

(65) Prior Publication Data

US 2014/0339080 A1 Nov. 20, 2014

(30) Foreign Application Priority Data

May 15, 2013 (DE) .................. 10 2013 208 939

(51) Int. Cl.
| | |
|---|---|
| *G01N 27/26* | (2006.01) |
| *G01N 7/00* | (2006.01) |
| *G01N 21/00* | (2006.01) |
| *G01N 27/00* | (2006.01) |
| *G01N 31/00* | (2006.01) |
| *G01N 33/00* | (2006.01) |
| *G01N 27/414* | (2006.01) |
| *G01N 27/407* | (2006.01) |

(52) U.S. Cl.
CPC ..... *G01N 27/4141* (2013.01); *G01N 27/4074* (2013.01)

(58) Field of Classification Search
CPC .......... G01N 27/26; G01N 7/00; G01N 21/00; G01N 27/00; G01N 31/00; G01N 33/00
USPC ........ 422/83, 88, 90, 98; 204/421, 424, 425, 204/426, 431
See application file for complete search history.

(56) References Cited

U.S. PATENT DOCUMENTS

| | | | | | |
|---|---|---|---|---|---|
| 4,025,412 | A | * | 5/1977 | LaConti ................. | 204/424 |
| 4,296,148 | A | * | 10/1981 | Friese .................. | 427/125 |
| 4,798,693 | A | * | 1/1989 | Mase et al. ............. | 264/44 |
| 5,272,871 | A | * | 12/1993 | Oshima et al. ........... | 60/274 |
| 5,879,526 | A | * | 3/1999 | Dietz et al. ............. | 204/425 |
| 6,246,159 | B1 | * | 6/2001 | Dejugnac et al. ......... | 310/358 |
| 8,603,699 | B2 | * | 12/2013 | Ito et al. ............... | 429/497 |
| 2004/0214069 | A1 | * | 10/2004 | Seabaugh et al. ......... | 429/40 |
| 2006/0280998 | A1 | * | 12/2006 | Ying et al. .............. | 429/40 |
| 2009/0290407 | A1 | * | 11/2009 | Mouli .................. | 365/158 |
| 2010/0112408 | A1 | * | 5/2010 | Yang et al. ............. | 429/33 |
| 2013/0192989 | A1 | * | 8/2013 | Fix et al. .............. | 204/424 |
| 2014/0214069 | A1 | * | 7/2014 | Franklin ............... | 606/194 |

FOREIGN PATENT DOCUMENTS

| | | |
|---|---|---|
| DE | 199 41 051 A1 | 3/2001 |
| DE | 10 2009 029 621 A1 | 3/2011 |
| DE | 10 2012 201 304 A1 | 8/2013 |

OTHER PUBLICATIONS

Sone et al.; Proton Conductivity of Nafion 117 as Measured by a Four-Electrode AC Impedance Method; Journal of The Electrochemical Society; Apr. 1996; pp. 1254-1259; vol. 143, Issue No. 4.

* cited by examiner

*Primary Examiner* — Brian J Sines
(74) *Attorney, Agent, or Firm* — Maginot, Moore & Beck LLP

(57) ABSTRACT

A sensor device for detecting and/or measuring gases includes two electrodes. A thin-layered proton-conductive material is fitted between the two electrodes. The gas can be detected and/or measured by a proton gradient that arises due to different gas concentrations.

15 Claims, 1 Drawing Sheet

MICROMECHANICAL SENSOR DEVICE

This application claims priority under 35 U.S.C. §119 to patent application number DE 10 2013 208 939.2, filed on May 15, 2013 in Germany, the disclosure of which is incorporated herein by reference in its entirety.

BACKGROUND

The present disclosure relates to a micromechanical sensor device, in particular for measuring and detecting gases.

Sensor devices for measuring and detecting gases are known e.g. from DE 199 41 051. A sensor element for determining the oxygen concentration is proposed in said document.

SUMMARY

It is therefore an object of the present disclosure to provide a novel, improved sensor device. This is achieved by means of a device according to the present disclosure. Accordingly, a sensor device for measuring and/or detecting is proposed, comprising:
a first micromechanical electrode;
a second micromechanical electrode; and
a thin-layered ion-conductive material which is embedded between the first electrode and second electrode.

In this case, the ion-conductive material has a conductivity in relation to positively charged ions, in particular protons, in relation to negatively charged ions. In the context of this application, this property should also be understood under the term "proton-conductive". That is to say, in other words, that the term "proton-conductive" in the sense of the present disclosure means and/or encompasses in particular materials that are able to conduct protons ($H^+$) while the conductivity in relation to other ions (e.g. oxygen ions) is greatly inhibited.

Surprisingly, it has been found that it is thus possible, in a simple manner, to detect gases and/or to measure the concentration thereof. In particular, at least one of the following advantages can be achieved by means of the method according to the disclosure in most applications:
the device is suitable for many purposes on account of its miniaturization,
depending on the specific configuration, the device can be used for a multiplicity of gases,
the simple construction of the device enables cost-effective manufacture The measurement and/or detection is effected in this case e.g. in such a way that the sensor device separates a reference gas space from a gas atmosphere to be analyzed. If there is a difference in concentration with regard to the measurement gas in the reference gas space and the gas atmosphere, a proton flow from the gas space having a higher concentration in the direction of the gas space having lower concentration arises by means of the electrodes. This potential can then be measured. Alternatively, as a result of a voltage being externally applied to the electrodes, protons can be pumped through the thin-layered proton-conductive material, provided that one of the two gas spaces contains hydrogen or hydrogen-containing gas species, which can thus be detected in this way.

The gas to be detected and/or measured preferably is or contains hydrogen or a hydrogen-containing compound such as a hydrocarbon or ammonia.

The term "micromechanical" in the sense of the present disclosure encompasses and/or means in particular that the sensor device can be processed with the aid of established production processes from microsystems engineering. In this case, proven etching and structuring methods (e.g. KOH etching process, trench processes, lithography processes, etc.) can be used to produce cavities, membranes and further geometries required for the sensor device.

The term "thin-layered" in the sense of the present disclosure encompasses and/or means in particular thin layers having a thickness approximately in the three-digit nanometers range, as explained in even greater detail below.

In accordance with one preferred embodiment of the present disclosure, the thickness of the thin-layered ion-conductive material is from greater than or equal to 50 nm to less than or equal to 1500 nm, preferably greater than or equal to 100 nm to less than or equal to 1000 nm, more preferably greater than or equal to 200 nm to less than or equal to 800 nm. These thicknesses have proved worthwhile in practice.

In accordance with one preferred embodiment of the present disclosure, the ion conductivity, in particular the proton conductivity, of the thin-layered proton-conductive material is greater than or equal to $10^{-8}$ S/cm, more preferably greater than or equal to $10^{-5}$ S/cm, more preferably greater than or equal to $10^{-3}$ S/cm. It has been found in practice that the usability and quality of the sensor device increase greatly starting from these proton conductivities, and so these have proved worthwhile in practice.

In this case, the proton conductivity is measured e.g. by means of impedance spectroscopy (J. Electrochem. Soc., Vol. 143, No. 4, 1996, page 1254-1259).

In accordance with one preferred embodiment, the thin-layered proton-conductive material predominantly consists of a material selected from the group of polymers, preferably Nafion, and/or from the group of ceramics, in this case preferably yttrium oxide ($Y_2O_3$), perovskites such as e.g. barium zirconate or acceptor-doped oxides/perovskites (e.g. Nd:$BaCeO_3$, Y:$SrZrO_3$, Y:$SrCeO_3$), or mixtures of these materials.

In this case, the term "predominantly" means greater than or equal to 90% by weight, more preferably greater than or equal to 95% by weight, more preferably greater than or equal to 98% by weight, and most preferably greater than or equal to 99% by weight.

In accordance with one preferred embodiment, one of the two electrodes, preferably both electrodes, is/are embodied in a porous fashion. This has proved to be advantageous for the present disclosure since this improves flowing of the gas onto the sensor device and in particular the thin-layered proton-conductive material.

The cross-section of the pores can be in the range of from a few nanometers up to tens or hundreds of micrometers. Metals having a catalytic effect such as e.g. Pt, Pd, Au, Ni are preferably appropriate as electrode materials, that is to say that, in accordance with one preferred embodiment, one or both electrodes predominantly consist(s) of a material selected from the group Pt, Pd, Au, Ni or mixtures thereof.

In accordance with one preferred embodiment, the sensor device furthermore comprises a micromechanical carrier substrate, having a porosified region, above which the electrodes and the thin-layered proton-conductive material are arranged. This has proved worthwhile in practice since in this way, on the one hand, the carrier substrate remains relatively stable, and on the other hand nevertheless enough gas to be detected and/or measured passes to the sensor device.

In accordance with one preferred embodiment, the thin-layered proton-conductive material is coated at least partly on one or both sides with a proton-conductive thin film in order to protect the thin-layered proton-conductive material against corrosion.

In this case, thin films having a thickness of greater than or equal to 1 nm to less than or equal to 100 nm, preferably less than or equal to 10 nm, are preferably used.

Preferably, the proton-conductive thin film predominantly consists of a material selected from the group comprising yttrium-doped zirconium oxide, aluminum oxide, hafnium oxide, cerium oxide, tantalum oxide, or mixtures thereof.

In accordance with one preferred embodiment, the sensor device furthermore comprises an open cavity for defining a membrane region, wherein one of the electrodes runs through the cavity.

Physical deposition methods such as sputtering, laser ablation, or chemical deposition methods such as CVD (Chemical Vapor Deposition) and atomic layer deposition are appropriate as production methods for the sensor devices (or, in the case of more complex devices, that part of the sensor device which is according to the disclosure).

Sensor devices of this type can be used e.g. in fire alarm systems, exhaust gas sensors in the motor vehicle sector, or safety systems for monitoring fuel cells or automotive exhaust gas systems.

The abovementioned and the described components which are to be used according to the disclosure and are described in the exemplary embodiments are not subject to any particular exceptional conditions in terms of their size, shaping, material selection and technical configuration, and so the selection criteria known in the field of application can be applied without restriction.

Further details, features and advantages of the subject matter of the disclosure are evident from the following description of the drawings and of an exemplary embodiment of the method according to the disclosure.

DETAILED DESCRIPTION

Figure 1:
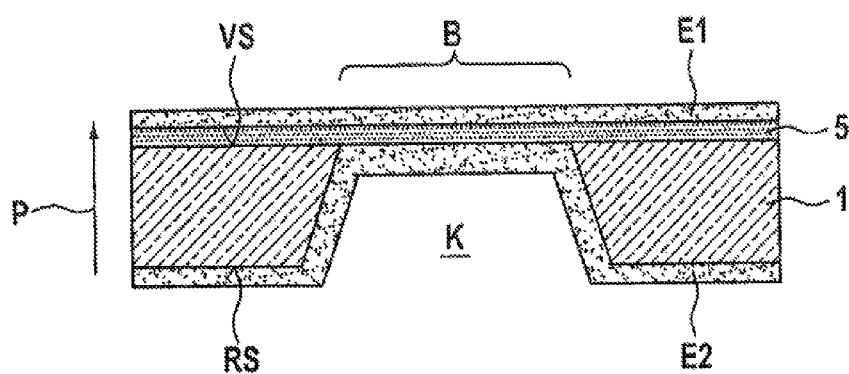
FIG. 1 shows a highly schematic partial cross-sectional view of a sensor device in accordance with one embodiment of the disclosure.

FIG. 1 shows a highly schematic partial cross-sectional view of a sensor device in accordance with one embodiment of the disclosure. As can be seen in FIG. 1, the sensor device has a carrier substrate 1 having a front side VS and a rear side RS. In this case, the carrier substrate 1 preferably consists of a material which can be processed/structured by semiconductor processes. "Traditional" semiconductors such as silicon, gallium arsenide, silicon carbide, gallium nitride, but also technical glasses such as e.g. Foturan are conceivable here. A cavity K is provided in the carrier substrate 1, said cavity extending from the rear side RS as far as the front side VS and defining a measurement region B. In this case, the thin-layered proton-conductive material 5 is applied in such a way that it covers the cavity and the peripheral region thereof. It is further surrounded by two electrodes E1 and E2. Overall, this region of the sensor device forms a simple Nernst cell.

A measurement method will be explained briefly on the basis of the example of hydrogen as measurement gas.

The sensor device is configured (not shown in FIG. 1) such that the front side VS faces the analyte gas space, while the rear side RS forms part of the reference gas space (which is preferably closed off, of course, relative to the surroundings). The electrodes E1, E2 comprises platinum, for example, about which it is known that it can store hydrogen in large amounts and can also catalyze reactions with hydrogen. By means of the electrodes E1, E2, protons are then incorporated into the thin-layered proton-conductive material 5, to be precise depending on the concentration of the hydrogen. If there is then a concentration gradient between the analyte gas space and the reference gas space (from which the hydrogen concentration must be known accurately, of course), a potential will build up which can be measured by means of the electrodes E1, E2. A similar method arises if e.g. hydrogen-containing gases such as hydrocarbons or $NH_3$ are intended to be measured. Here as well protons are incorporated into the thin-layered proton-conductive material 5.

Figure 2:
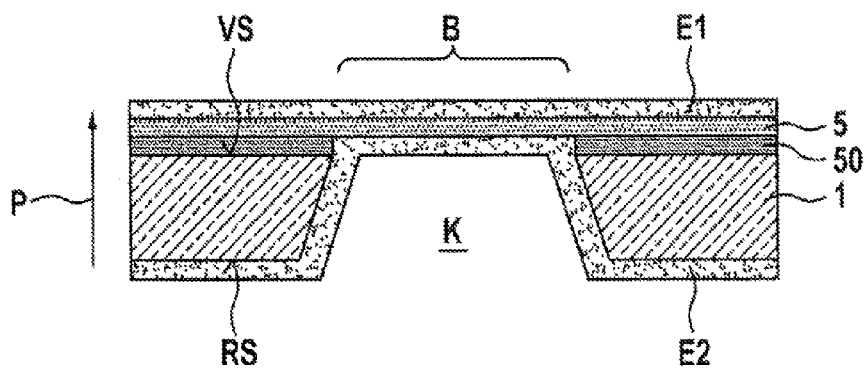
FIG. 2 shows a highly schematic partial cross-sectional view of a sensor device in accordance with a second embodiment of the disclosure.

FIG. 2 shows a modification of the cell from FIG. 1, to be precise in such a way that a proton-conductive thin film 50 is applied on one side of the thin-layered proton-conductive material 5. Said thin film 50 additionally protects the thin-layered proton-conductive material 5 against corrosion and can—not shown in the figures—also be applied in the measurement region and on both sides; in this respect, this is one preferred embodiment of the disclosure.

What is claimed is:

1. A sensor device for measuring and/or detecting gases, comprising:
   a first micromechanical electrode;
   a second micromechanical electrode; and
   a thin-layered ion-conductive material embedded between the first electrode and second electrode wherein the thin-layered ion-conductive material has a thickness that is greater than or equal to 50 nm and less than or equal to 1500 nm,
   wherein the thin-layered ion-conductive material has a higher conductivity in relation to positively charged ions than in relation to negatively charged ions.

2. The sensor device according to claim 1, wherein the thin-layered ion-conductive material has a thickness that is greater than or equal to 100 nm and less than or equal to 1000 nm.

3. The sensor device according to claim 1, wherein the thin-layered ion-conductive material has a conductivity in relation to positively charged ions that is greater than or equal to $10^{-8}$ S/cm.

4. The sensor device according to claim 1, wherein the thin-layered ion-conductive material is predominantly made of a material selected from polymers and/or from ceramics, perovskites, acceptor-doped oxides/perovskites, and mixtures of these materials.

5. The sensor device according to claim 1, wherein at least one of the first micromechanical electrodes and the second micromechanical electrodes is porous.

6. The sensor device according to claim 1, wherein at least one of the first micromechanical electrodes and the second micromechanical electrodes is predominantly made of a material selected from Pt, Pd, Au, Ni and mixtures thereof.

7. The sensor device according to claim 1, further comprising:
   a micromechanical carrier substrate having a porosified region, wherein the first micromechanical electrode, the second micromechanical electrode, and the thin-layered ion-conductive material are arranged above the porosified region.

8. The sensor device according to claim 1, wherein:
the thin-layered ion-conductive material is coated at least partly on at least one side with an ion-conductive thin film, and
the ion-conductive thin film has a higher conductivity in relation to positively charged ions than in relation to negatively charged ions.

9. The sensor device according to claim 8, wherein the ion-conductive thin film has a thickness that is greater than or equal to 1 nm and less than or equal to 100 nm.

10. The sensor device according to claim 1, further comprising:
an open cavity configured to define a membrane region, wherein the second micromechanical electrodes runs through the cavity.

11. The sensor device according to claim 3, wherein the conductivity in relation to positively charged ions is a proton conductivity.

12. The sensor device according to claim 4, wherein the polymer is Nafion.

13. The sensor device according to claim 4, wherein the ceramic is yttrium oxide ($Y_2O_3$).

14. The sensor device according to claim 4, wherein the perovskite is barium zirconate.

15. The sensor device according to claim 4, wherein the acceptor-doped oxide/perovskite is one of $Nd:BaCeO_3$, $Y:SrZrO_3$, and $Y:SrCeO_3$.

* * * * *